United States Patent [19]

Garfinkel et al.

[11] Patent Number: 5,462,873
[45] Date of Patent: Oct. 31, 1995

[54] DNA FOR USE IN A SIMPLE METHOD FOR DETECTING INHIBITORS OF RETROTRANSPOSITION

[75] Inventors: David J. Garfinkel, Frederick; M. Joan Curcio, Keedysville, both of Md.

[73] Assignee: The United States of America as represented by the Department of Health and Human Services, Washington, D.C.

[21] Appl. No.: 102,854

[22] Filed: Aug. 6, 1993

Related U.S. Application Data

[63] Continuation of Ser. No. 668,865, Mar. 13, 1991, abandoned.

[51] Int. Cl.⁶ .................... C12N 15/00; C07H 17/00
[52] U.S. Cl. ............... 435/254.2; 435/6; 435/252.3; 435/240.2; 435/320.1; 536/23.1
[58] Field of Search .................... 435/320.1, 255, 435/6, 29, 254.2

OTHER PUBLICATIONS

Heidmann, Odile and Thierry, Retrotransposition of a Mouse IAP Sequence Tagged with an Indicator Gene, *Cell*, Jan. 11, 1991, vol. 84, pp. 159–170.

Garfinkel, D. et al., Transposon Tagging Using Ty Elements in Yeast, *Genetics*, Sep., 1988, vol. 120, pp. 95–108.

Boeke, J. D. et al, A General Method for the Chromosomal Amplification of Genes In Yeast, *Science*, vol. 239, pp. 280–282.

Boeke, J. D. et al, Ty Elements Transpose through an RNA Intermediate, *Cell*, Mar. 1985, vol. 40, pp. 491–500.

Heidmann, T. et al., An Indicator Gene to Demonstrate Intracellular Transposition of Defective Retroviruses, *Proc. Natl. Acad. Sci. USA*, Apr. 1988, vol. 85, pp. 2219–2223.

*Primary Examiner*—Mindy B. Fleisher
*Attorney, Agent, or Firm*—Needle & Rosenberg

[57] ABSTRACT

The present invention relates, in general, to a DNA segment. In particular, the present invention relates to a DNA segment comprising a selectable marker gene, a DNA segment comprising a selectable marker gene inserted into a retrotransposon, cells containing these DNA segments, and methods of using these DNA segments and cells.

17 Claims, 5 Drawing Sheets

DNA FOR USE IN A SIMPLE METHOD FOR DETECTING INHIBITORS OF RETROTRANSPOSITION

This application is a continuation of application Ser. No. 07/668,865, filed Mar. 13, 1991, now abandoned.

BACKGROUND OF THE INVENTION

1. Field of the Invention

The present invention relates, in general, to a DNA segment. In particular, the present invention relates to a DNA segment comprising a selectable marker gene, a DNA segment comprising a selectable marker gene inserted into a retrotransposon, cells containing these DNA segments, and methods of using these DNA segments.

2. Background Information

Ty elements of *Saccharomyces cerevisae* are retrotransposons that are similar to retroviral proviruses (Boeke, J.D. (1989) in *Mobile DNA*, eds., Berg, D. E. & Howe, M. M. (Am. Soc. Microbiol, Washington), pp. 335–374). Retrotransposition is a replicative process involving reverse transcription of Ty mRNA and integration of Ty cDNA into the genome (Boeke et al. *Cell* (1985) 40: 491–500). Ty1 elements are the most common insertional mutagen and comprise the most numerous family of the four Ty element classes, with about 25–30 copies of Ty1 per haploid genome (Cameron, et al. *Cell* (1979) 16:739–751; Curcio, M. J. et al. *Mol. Gen. Genet.*(1990) 220:213–221). Despite the fact that Ty1 RNA accounts for 1% of total yeast RNA (Curcio, M. J. et al. *Mol. Gen. Genet.* (1990) 220:213–221), the rate of transposition is quite low (Giroux, C. N., et al. *Mol. Cell. Biol.* (1988) 8:978–981; Boeke, J. D. et al. *Mol. Cell. Biol.* (1986) 6:3575– 3581; Paquin, C. E. et al. *Mol. Cell. Biol.* (1986) 4:70–79). Several modulators of transposition have been described. For example, Ty transposition is stimulated at temperatures below 30° C. (Paquin, C. E., et al. *Science* (1984) 226:53– 55), by exposure of the cells to ultraviolet irradiation or 4-nitroquinoline 1-oxide (Bradshaw, V. A., et al. *Mol. Gen. Genet.* (1988) 218:465–474), or in a rad6 mutant background (Picologlou, et al. *Mol. Cell. Biol.* (1990) 10: 1017–1022). Mutations in the SPT3 gene alter the initiation of Ty1 transcription (Winston, et al. *Cell* (1984) 39:675– 682) and abolish retrotransposition of chromosomal Ty1 elements (Boeke, J. D. et al. *Mol. Cell. Biol.* (1986) 6:3575–3581). These modulators of retrotransposition were identified by their effect on the frequency of Ty insertions into specific loci and not into the genome as a whole. As a result, it can be difficult to determine whether the modulators alter Ty elements directly or the target locus (Picologlou, et al. *Mol. Cell. Biol.* (1990) 10: 1017–1022).

A tremendous induction in the rate of Ty1 transposition is achieved by expressing an active Ty element, Ty1-H3, from the inducible GAL1 promoter (Boeke et al. *Cell* (1985) 40: 491–500). The pGTy1-H3 element has been marked with selectable genes such as a bacterial gene for neomycin resistance (Boeke, et al. *Science* (1988) 239:280–282) and the yeast HIS3 gene (Garfinkel, et al. *Genetics* (1988) 120:95–108). Phenotypic detection of retrotransposition events in the transposition-induction system requires loss of the pGTy plasmid. In addition, transposition of the marked Ty1 element can only be detected when it is induced to a level that exceeds the rate of homologous recombination among Ty elements (Roeder, et al. *Proc. Natl. Acad. Sci. USA* (1982) 79:5621–5625; Roeder, et al. *Mol. Cell. Biol.* (1984) 4:703–711).

SUMMARY OF THE INVENTION

It is a general object of this invention to provide a DNA segment.

It is a specific object of this invention to provide a DNA segment comprising a selectable marker gene.

It is another object of the invention to provide a DNA segment comprising a selectable marker gene inserted into a retrotransposon.

It is a further object of the invention to provide a cell that contains the above mentioned DNA segments.

It is yet another object of the invention to provide a method of selecting cells wherein retrotransposition has occured.

It is a further object of the invention to provide a method of detecting a compound capable of inhibiting retroviral replication or retrotransposition.

It is another object of the invention to provide a method of selecting a mutant retrotransposon that is resistant to a compound capable of inhibiting retroviral replication or retrotransposition.

Further objects and advantages of the present invention will be clear from the description that follows.

In one embodiment, the present invention relates to a DNA segment comprising a selectable marker gene containing an intron inserted into a translatable sequence coding for the marker gene wherein the intron is present in an antisense orientation relative to transcription of the marker gene.

In another embodiment, the present invention relates to a DNA segment comprising a selectable marker gene inserted into a retrotransposon wherein the marker gene contains an intron inserted into a translatable sequence coding for the marker gene and the intron is in an antisense orientation relative to transcription of the marker gene and in a sense orientation relative to transcription of the retrotransposon.

In a further embodiment, the present invention relates to cells that contain the above mentioned DNA segments.

In another embodiment, the present invention relates to a method of selecting cells wherein retrotransposition of the above mentioned retrotransposon has occured comprising:

(1) placing the cells onto selectable media, (2) culturing the cells, and (3) selecting for colonies of the cells which grow.

In another embodiment, the present invention relates to a method of detecting a compound capable of inhibiting retroviral replication or retrotransposition in the above mentioned cells comprising:

(1) placing the cells onto selectable media, (2) exposing the cells to the compound, (3) culturing the cells, and (4) determining if growth of the cells is inhibited.

In another embodiment, the present invention relates to a method of selecting a mutant retrotransposon that is resistant to a compound capable of inhibiting retroviral replication or retrotransposition in the above-described cells comprising:

(1) placing the cells onto selectable media, (2) exposing the cells to the compound, (3) culturing the cells, and (4) selecting cells whose growth is not inhibited by the compound.

DETAILED DESCRIPTION OF THE INVENTION

Figure 1A:
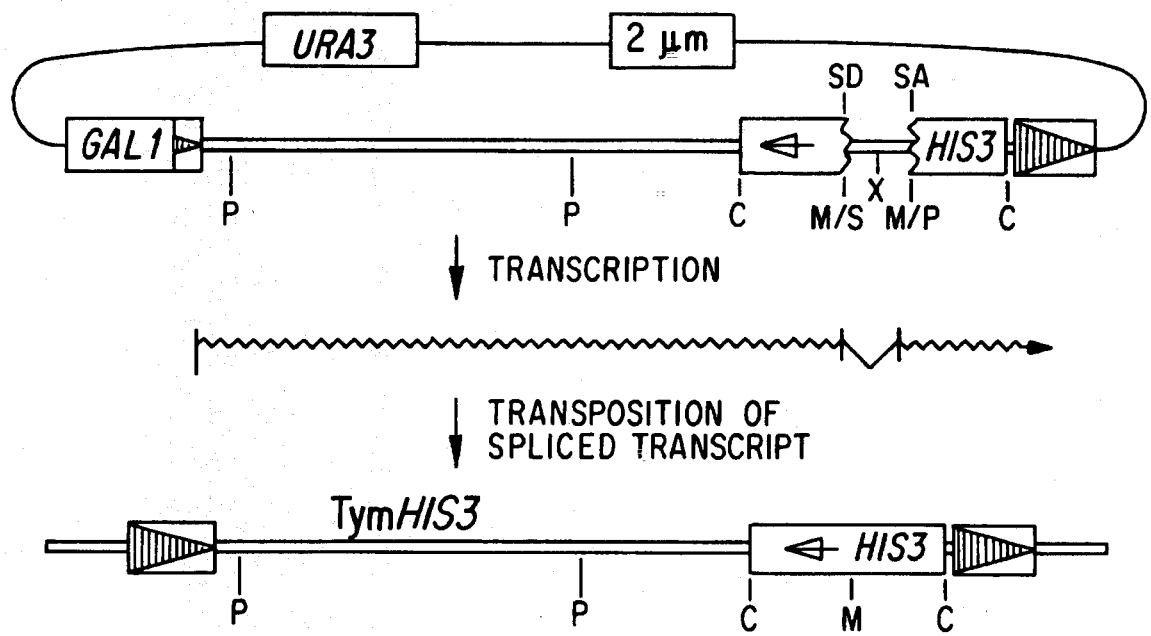
FIG. 1. Genetically marked derivatives of plasmid pGTy1-H3. (A) Structure of plasmid pGTy1-H3mHIS3AI. The boxed arrow heads represent the Ty1 long terminal repeats and the direction of Ty1 transcription. The shaded box represents the yeast HIS3 gene and the enclosed arrow indicates its direction of transcription. AI sequences, represented by the broken line, are in the antisense orientation relative to the HIS3 gene but in the sense orientation relative to Ty1-H3. The Ty1-H3mHIS3AI transcript is represented by the wavy line. Splicing is indicated by vertical lines in the transcript. TymHIS3 is the spliced and transposed copy of the marked element. (B) Structure of the GAL1-Ty1 fusion element contained in plasmid pGTy1-H3HIS3mAI. In this plasmid, the HIS3AI gene is transcribed in the same direction as the Ty1 element, and the intron, which is in the antisense orientation relative to both Ty1-H3 and HIS3 transcription, is unspliceable. (C) The element contained on pGTy1-H3mHIS3. The abbreviations used are: GAL1, yeast GAL1 promoter; SD, splice donor; SA, splice acceptor; URA3, yeast URA3 gene; 2 µm, yeast 2-µm origin of replication; P, Pvu II; C, Cla I; X, XbaI; M, Msc l; M/S, Msc I/SnaBI hybrid sites; M/P, Msc I/Pvu II hybrid sites.

The present invention relates to DNA segments comprising a selectable marker gene or a selectable marker gene inserted into a retrotransposon.

More specifically, the present invention relates to DNA segments comprising a selectable marker gene wherein the selectable marker gene contains an intron inserted into a translatable sequence coding for the marker gene wherein the intron is present in an antisense orientation relative to transcription of the marker gene. In one preferred embodiment, the selectable marker gene is HIS3 and contains the above-described intron (for example—HIS3AI).

In another embodiment, the present invention relates to a DNA segment comprising a selectable marker gene inserted into a retrotransposon wherein the marker gene contains an intron inserted into a translatable sequence coding for the marker gene and the intron is in an antisense orientation relative to transcription of the marker gene and in a sense orientation relative to transcription of the retrotransposon. In one preferred embodiment, the intron is an artificial intron (preferably, a yeast artificial intron or more specifically, a 104-base-pair artificial yeast intron contained on a PvuII-SnaB1 fragment). In another preferred embodiment, the selectable marker gene is HIS3 and contains the above-described intron (examples include: HIS3AI, Ty1-H3mHIS3A1, and pGTy1-H3mHIS3A1). In a further preferred embodiment, the retrotransposon is a yeast retrotransposon (for example—Ty1).

In a further embodiment, the present invention relates to a cell containing the above described DNA segments (suitable host cells include procaryotes (such as bacteria) and both lower eucaryotes (for example yeast) and higher eucaryotes (for example, mammalian cells). Introduction of the DNA segment into the host cell can be affected using methods known in the art.

In another embodiment, the present invention relates to a method of selecting the above described cells wherein retrotransposition of the retrotransposon has occured comprising:

(1) placing the cells onto selectable media,
(2) culturing the cells, and
(3) selecting for colonies of the cells which grow.

This method has several advantages over other transposition-detection systems used (Boeke et al. *Cell* (1985) 40: 491–500; Boeke, et al. *Science* (1988) 239:280–282; Garfinkel, et al. *Genetics* (1988) 120:95–108). Since the reporter gene is only phenotypically activated in retrotransposed copies of the marked element, transposition can be scored in the presence of the original marked element. Moreover, selection for the transposition of chromosomal elements can be performed in the absence of insertions into specifics targets. This feature will be extremely useful in identifying genes that modulate Ty transposition. An advantage of the HIS3AI reporter gene is that splicing of the reverse transcript results in the creation of an Msc I site, allowing presence of the exact splice junction to be confirmed at the nucleotide level in a Southern blot. Additionally, other rearrangements that phenotypically activate HIS3AI occur at a very low frequency.

In a further embodiment, the present invention relates to a method of detecting a compound (for example—hydroxyurea) capable of inhibiting retroviral replication or retrotransposition in the above described cells comprising:

(1) placing the cells onto selectable media,
(2) exposing the cells to said compound,
(3) culturing the cells, and
(4) determining if growth of the cells is inhibited.

The above described method can be also be used to detect compounds that affect splicing. Reagents of this type could be identified in a secondary screen.

In a further embodiment, the present invention relates to a method of selecting a mutant retrotransposon that is resistant to a compound capable of inhibiting retroviral replication or retrotransposition in the above-described cells comprising:

(1) placing the cells onto selectable media, (2) exposing the cells to the compound, (3) culturing the cells, and (4) selecting cells whose growth is not inhibited by the compound.

The present invention is described in further detail in the following non-limiting examples.

EXAMPLES

The following protocols and experimental details are referenced in the examples that follow:

Plasmid Constructions.

Figure 1B:
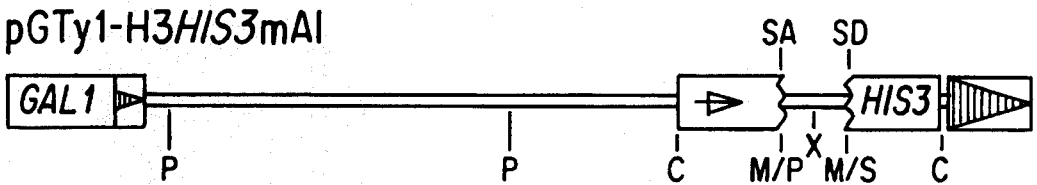
Figure 1C:
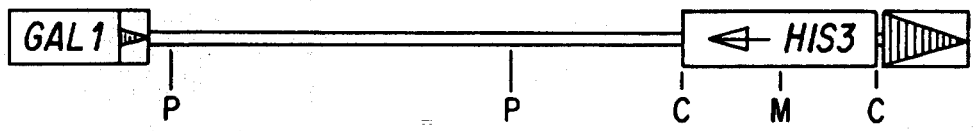

The HIS3AI indicator gene was constructed by cloning a 104-base-pair artificial yeast intron (AI), contained on a Pvu II-SnaBI fragment (Yoshimatsu, et al. *Science* (1989) 244:1346–1348), into the blunt-end Msc I site of HIS3 carried on pCLA12HIS3 (Garfinkel, et al. *Genetics* (1988) 120:95–108; Struhl, K. *Nucleic Acids. Res.* (1985) 13:8587–8601), to form pCLA12HIS3AI. The predicted intron-exon junctions were confirmed by DNA sequencing (Sanger, et al. *Proc. Natl. Acad. Sci.* (1977) 74:5463–5467). A HIS3AI Cla I fragment was cloned into the Cla I site of pGTy1-H3CLA (Garfinkel, et al. *Genetics* (1988) 120:95–108) in both orientations. The resulting plasmids have HIS3AI in either the sense or antisense orientation relative to Ty1-H3 transcription and are called pGTy1-H3mHIS3AI or pGTy1-H3HIS3mAI, respectively (FIG. 1, A and B). Plasmid pGTy1-H3mHIS3 was made by inserting the Cla I fragment of pCLAI2HIS3 into the Cla I site of pGTy1-H3CLA (FIG. 1C).

Yeast Strains and Media.

The yeast strains used are GRF167 (MATα, ura3-167, his3-Δ200, GAL), and an isogenic Spt3 derivative, DG789, both of which contain a complete HIS3 deletion (Boeke et al. *Cell* (1985) 40: 491–500; Struhl, K. *Nucleic Acids. Res.* (1985) 13:8587–8601). Strains JC234, JC242, JC246, and JC271 are congenic derivatives of GRF167 that contain different unspliced TymHIS3AI insertions. These strains were isolated after galactose induction of plasmid pGTy1-H3mHIS3AI in strain GRF167 and subsequent segregation of the pGTy plasmid. Standard yeast media were prepared as described by Sherman et al. (Sherman, et al. *Laboratory Course Manual for the Methods in Yeast Genetics* (Cold Spring Harbor Lab., Cold Spring Harbor, N.Y.) (1986)).

Transposition Efficiencies.

To determine the fraction of cells that sustain a marked transposition in strains containing pGTy1-H3HIS3AI plasmids, cultures were inoculated at low densities and grown to saturation at 20° C. in SC-ura galactose (Sherman, et al. *Laboratory Course Manual for the Methods in yeast Genetics* (Cold Spring Harbor Lab., Cold Spring Harbor, N.Y.) (1986)) to induce transposition or in SC-ura glucose (Sherman, et al. *Laboratory Course Manual for the Methods in Yeast Genetics* (Cold Spring Harbor Lab., Cold Spring Harbor, N.Y.) (1986)). A portion of each culture was then plated onto SC-his glucose plates (Sherman, et al. *Laboratory Course Manual for the Methods in yeast Genetics* (Cold Spring Harbor Lab., Cold Spring Harbor, N.Y.) (1986)) and grown at 30° C. to end the transposition induction and score histidine prototrophs. The cultures were titered on YEPD plates.

Southern Blot Analysis of Transposition-Induced Strains.

Strains containing pGTy plasmids were grown for 5 days at 20° C. on SC-ura galactose plates. Independent colonies were recovered and processed for Southern blot analysis with a randomly labeled HIS3 or Ty probe as described (Curcio, M. J. et al. *Mol. Gen. Genet.* (1990) 220:213–221).

Analysis of Genomic TymHIS3AI Elements.

Transposition rates were determined by the method of Lea, et al. *J. Genet.* (1949) 49:264–285. Between 7 and 11 cultures inoculated with ≈200 cells were grown to saturation at 20° C. in YEPD and then plated onto SC-his glucose medium at 30° C. Three cultures of each strain were titered on YEPD plates. Northern blot analysis was performed with excess $^{32}$P-labeled HIS3, Ty1, and PYK1 RNA probes, as described (Curcio, M. J. et al. *Mol. Gen. Genet.* (1990) 220:213–221).

EXAMPLE 1

Construction of a Reporter Gene for Retrotransposition.

A reporter gene for retrotransposition that consists of an AI interrupting the coding sequences of HIS3 was designed. The intron is a portable cassette containing all of the cis-acting sequences required for splicing without any flanking exon sequences (Yoshimatsu, et al. *Science* (1989) 244:1346–1348). The AI was inserted into the HIS3 coding sequence in an antisense orientation, thereby inactivating HIS3 and destroying an Msc I site. To form Ty1-H3mHIS3AI (the "m" indicates the presence of HIS3 gene sequences on the minus strand of Ty1-H3), the HIS3AI gene was placed on the minus stand of Ty1-H3, such that transcription of HIS3AI is opposite of Ty transcription (FIG. 1A). Since the intron is in the antisense orientation relative to the HIS3 transcript, it is in the correct orientation to be precisely removed from the Ty1-H3 RNA transposition intermediate by splicing. Therefore, colonies harboring transposed TymHIS3 elements can be identified by growth on medium lacking histidine. Restoration of the Msc I site in transposed copies of TymHIS3 can be easily detected by Southern blot analysis, confirming the presence of the correct splice junction.

As a control for DNA recombination events that confer a His$^+$ phenotype, a derivative of Ty1-H3 containing HIS3AI in the same transcriptional orientation as Ty1-H3 (Figure 1B) was constructed. The AI in this element, Ty1-H3HIS3mAI, is in an antisense orientation relative to both the Ty1 and HIS3 transcripts. (The "m" signifies the presence of AI on the minus strand of Ty1-H3.) Therefore, both the starting transposon and transposed copies of TyHIS3mAI should retain the intron and remain His$^+$ if splicing of the retrotransposition intermediate is required for recreation of a functional HIS3 gene.

EXAMPLE 2

Galactose Induction of pGTy1-H3mHIS3AI Transcription Results in High Levels of Retrotransposition.

To determine whether HIS3AI was an indicator of Ty retrotransposition, pGTy plasmids containing the Ty1-H3mHIS3AI or Ty1-H3HIS3mAI elements were introduced into yeast strain GRF167 and assayed for transposition (Table 1). The transformants were phenotypically His$^-$, indicating that the HIS3AI gene cannot confer a His$^-$ phenotype in the absence of Ty1-H3 transcription. Cells were grown in liquid medium containing galactose and then plated onto SC-his glucose medium to end transposition induction and select for His$^+$ colonies. After transposition induction of pGTy1-H3m-HIS3AI in isogenic SPT3 (Table 1) or spt3 strains (data not shown), almost 2% of the cells became His⁺. Transcription of the Ty1-H3mHIS3AI element from the GAL1 promoter is required for this high frequency of His⁺ reversion. When cells are grown on glucose, which represses pGTy transcription, His⁺ colonies appear at a frequency more than five orders of magnitude lower. The frequency of histidine prototrophs observed upon transposition induction of cells containing pGTy1-H3HIS3mAI is also more than five orders of magnitude lower than strains harboring pGTy1-H3mHIS3AI (Table 1). Therefore, splicing is required for the generation of histidine prototrophs. Thus these data show that the pGTy1-H3mHIS3AI element yields a high level of retrotransposition events in which the HIS3 gene is recreated by splicing.

To confirm that His⁺ revertants recovered after induction of pGTy1-H3mHIS3AI contained spliced TymHIS3 transpositions, 30 His⁺ colonies were analyzed by Southern blot hybridization (data not shown). All 30 colonies contained at least one integrated TymHIS3 element with bands predicted to be present only in precisely spliced TymHIS3 elements.

TABLE 1

Transposition induction of PGTy1-H3 marked with HIS3AI gene

| Ty marker | Carbon source | No. His⁺colonies/ culture | Mean transposition efficiency |
|---|---|---|---|
| mHIS3AI | Gal | 349,604,577 | $1.7 \times 10^{-2}$ |
| mHIS3AI | Glc | 0,1,1 | $2.5 \times 10^{-8}$ |
| HIS3mAI | Gal | 1,0,1 | $3.2 \times 10^{-8}$ |

Each measurement represents the results from one of the three cultures. The total number of colony-forming units was similar within each set of cultures; the average titers are (top to bottom): $3.4 \times 10^4$, $2.7 \times 10^7$, and $2.1 \times 10^7$. The mean transposition efficiency is the mean fraction of total colonies assayed that are His⁺.

EXAMPLE 3

Splicing Is Not Required for Ty1-H3mHIS3AI Transposition But Is Required for Generation of a His⁺ Phenotype.

To determine whether the intron was ever retained during retrotransposition, 24 Ura⁺ colonies were selected after transposition induction of pGTy1-H3mHIS3AI, and 5 were His⁺. After plasmid segregation, His⁺ and His⁻ colonies were analyzed by Southern blot analysis with a HIS3 probe (Table 2). Spliced elements were identified as those that recreated the HIS3 Msc I site and lacked the intronic Xba I site in a Pvu II/Msc I or Pvu II/Xba I digest (FIG. 1). Elements lacking the HIS3Msc I site but retaining the intron Xba I site were scored as unspliced. Twenty of the 24 colonies analyzed contained genomic copies of the HIS3-marked element. Eighteen of these harbored between one and six copies of the unspliced TymHIS3AI element. The 5 His⁺ colonies each contained one copy of the spliced Tym-HIS3 element. A mean number of 1.7 marked transposition events per colony was found and 5 of 40 (12.5%) transposed Ty elements had lost the intron. Transposition induction of cells containing pGTy1-H3-HIS3mAI resulted in 2.5 marked transpositions per isolate. All of these colonies were phenotypically His⁻, and all of the transposed TyHIS3mAI elements remained unspliced. The transposition frequencies of the Ty1-H3 derivatives marked with HIS3AI gene in both orientations were similar to the activity of the intron less pGTy1-H3mHIS3 element (Table 2) and to other marked pGTy1-H3 derivatives (Boeke, et al. *Science* (1988) 239:280–282; Garfinkel, et al. *Genetics* (1988) 120:95–108).

These data indicate that the intron in either orientation does not inhibit transposition, but splicing is required for histidine prototrophy.

TABLE 2

Mean number of marked transposition events per induced cell

| Plasmid | No. spliced elements per genome | No. unspliced elements per genome | No. total elements per genome |
|---|---|---|---|
| pGTy1-H3mHIS3AI | 0.2 (5/24) | 1.5 (35/24) | 1.7 (40/24) |
| pGTy1-H3HIS3mAI | 0 (0/16) | 2.5 (40/16) | 2.5 (40/16) |
| pGTy1-H3mHIS3 | N/A | N/A | 1.3 (26/20) |

Plasmids were analyzed in yeast strain GRF167. The values given are the mean number of bands hybridizing to a HIS3 probe on the appropriate Southern blot of transposition-induced colonies. The numbers in parentheses are the total number of junction fragment bands divided by the number of randomly selected transposition-induced colonies analyzed. N/A, not applicable.

EXAMPLE 4

Transposition of Chromosomal TymHIS3AI Elements Can Be Detected Phenotypically.

The ability to determine if transposition of individual chromosomal elements could be detected was provided by the above analysis. When several strains harboring unspliced TymHIS3AI elements but lacking the pGTy1-H3mHIS3AI plasmid were grown at 20° C. and then replica plated to SC-his medium at 30° C. His⁺ papillae appeared. In contrast, histidine prototrophs were not detected in strains harboring chromosomal TyHIS3mAI elements. The frequency of His⁺ reversion in several strains containing unspliced TymHIS3AI elements decreased more than 20-fold if the cells were grown at 30° C. or 36° C. relative to 20° C. and His⁺ reversion was reduced at least 100 times in isogenic spt3 derivatives of these strains (data not shown). The dependence of His⁺ reversion on known modulators of Ty1 transposition and on intron orientation strongly suggests that retrotransposition of genomic TymHIS3AI elements is being detected.

Figure 2:
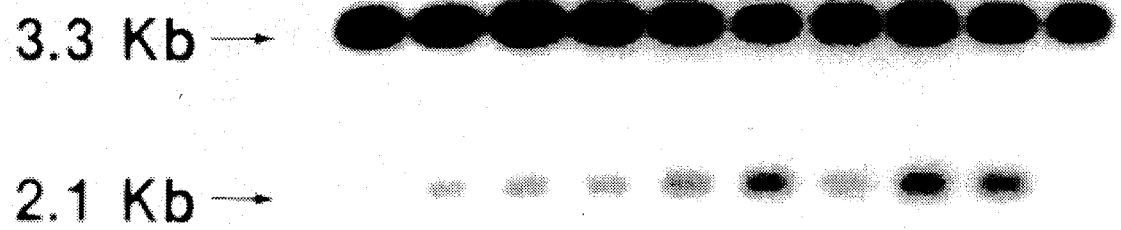
FIG. 2. Spontaneous His⁺ revertants of a strain harboring the chromosomal TymHIS3AI element contain dispersed copies of Tym-HIS3 with the intron precisely removed. Parental strain JC 242 (lanes 1 and 10) and eight His⁺ revertants derived from strain JC242 (lanes 2-9) are shown. DNA from each revertant strain was digested with Pvu II and Msc I and probed with HIS3. The 3.3-kb band is the junction fragment between the 3' end of the TymHIS3AI element and flanking sequence DNA. The 2.1-kb band is an internal fragment of TymHIS3 from the Pvu II site in Ty1 to the Msc I site in the spliced HIS3 gene. The dispersed bands are junction fragments between the HIS3 Msc I site and a site in 3' flanking sequence DNA.

To extend these observations, strain JC242, a His⁻ strain harboring one unspliced TymHIS3AI element, was used to generate eight His⁺ revertants. DNA from these strains was digested with Pvu II and Msc I and analyzed by Southern blot hybridization using a HIS3 probe (FIG. 2). The parental strain contains one 3.3-kilobase (kb) band because of the absence of an Msc I site in the unspliced HIS3AI gene. In the His⁺ revertants, this 3.3-kb band appears unaltered, suggesting that the His⁺ phenotype does not result from rearrangement of the HIS3AI gene within the original marked Ty1 element. However, the His⁺ colonies contain two new bands indicative of replicative transposition. In every case, a 2.1-kb band expected of an internal fragment from the Pvu II site in Ty1 to the Msc I site of the HIS3 gene is seen. The Msc I site within the HIS3 gene demonstrates that precise splicing has occurred in the process of TymHIS3 retrotransposition. Each His⁺ revertant also contains one other band of varied size. These bands represent junction fragments extending from the Msc I site in HIS3 to the next Pvu II or Msc I site in flanking sequences and are also suggestive of de novo transposition.

EXAMPLE 5

Rate of Transposition of Single Genomic Ty Elements.

The His⁺ reversion rate was calculated by the method of Lea and Coulson (*J. Genet.* (1949) 49:264–285) for four strains containing either one, two, or five to six genomic copies of the TymHIS3AI elements (Table 3). The rate of His+ reversion in these strains varies between $3.4 \times 10^{-9}$ and $1.6 \times 10^{-7}$ per generation per TymHIS3AI element present in the genome. To estimate the average rate of Ty transposition, the His+ reversion rates were converted to transposition rates by accounting for the splicing efficiency and the effects of the marker gene on transposition. Our estimate is based on the assumption that genomic TymHIS3AI transcripts are spliced at the same frequency as those from the pGTy plasmid (Table 2). Therefore, about one-eighth of the transposition events are detected as histidine prototrophs. To determine if the presence of the HIS3AI gene decreased the level of Ty1 transposition, the abilities of the unmarked pGTy1-H3 and the pGTy1-H3mHIS3AI elements to transpose in an spt3 mutant DG789 were compared (Table 4). These results suggest that the marker gene lowers the level of Ty transposition by a factor of 11. Therefore, the average His+ reversion rate was multiplied by a factor of 88 to obtain an estimated transposition rate of $3 \times 10^{-7}$ and $1 \times 10^5$ transposition events per Ty1 element per generation.

To determine whether the 50-fold variation in transposition rates might result from differences in transcript levels of individual TymHIS3AI elements, Northern blot hybridizations (FIG. 3) with total RNA from low and high-reverting strains JC234 (lane 1) and JC242 (lane 2) were performed. The results show that although the amount of total Ty RNA is similar, the level of TymHIS3AI RNA is much lower in strain JC234 than JC242.

TABLE 3

Rate of His+ reversion in yeast strains containing genomic TymHIS3AI elements

| Strain | No. of TymHIS3AI elements | Rate of His+ reversion ($\times 10^{-7}$) | Mean rate per TymHIS3AI element ($\times 10^{-7}$) |
|---|---|---|---|
| JC234 | 1 | 0.034 ± 0.029 | 0.034 |
| JC242 | 1 | 1.6 ± 0.5 | 1.6 |
| JC246 | 2 | 1.4 ± 0.2 | 0.7 |
| JC271 | 5-6 | 9.1 ± 3.2 | 1.5-1.8 |

Ura− His− colonies isolated after transposition induction of plasmid, pGTy1-H3mHIS3AI in strain GRF167. The number of TymHIS3AI elements was determined by Southern blot analysis. The rate of His+ reversion is expressed as mutations per cell per generation (means = 95% confidence interval).

TABLE 4

Relative transposition levels of pGTy1-H3 and pGTy1-H3mHIS3AI in spt3 mutant DG789

| Plasmid | No. of new bands hybridizing to a Ty1 probe | No. of colonies tested | Mean no. of transposition events |
|---|---|---|---|
| pGTy1-H3 | 40 | 16 | 3.5 |
| pGTy1-H3mHIS3AI | 3 | 13 | 0.23 |

EXAMPLE 6

Single-Step Assay for Retrotransposition.

Figure 4:
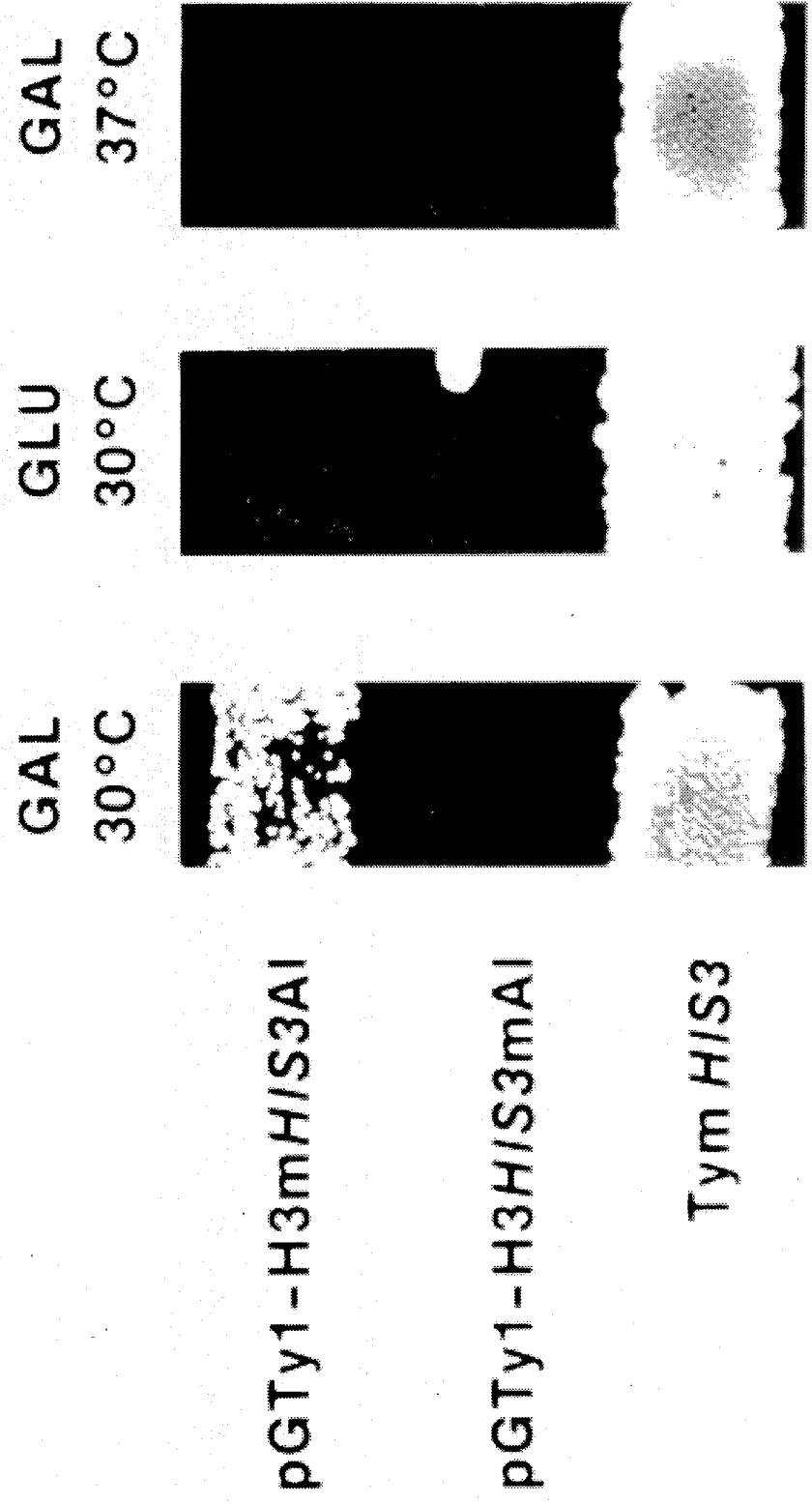
FIG. 4. Single-step assay for transposition of Ty1 marked with the retrotransposition reporter gene. Strains containing pGTy1-H3 marked with HIS3AI in the spliceable (pGTy1-H3mHIS3AI) or unspliceable (pGTy1-H3HISmAI) orientation or a chromosomal copy of TymHIS3 were replica plated onto SC-ura galactose (Gal) or glucose (Glu) plates containing limiting amounts of histidine (0.3 µM) and grown at 30° C. or 37° C.

Another application of the HIS3AI reporter gene is its use in a single-step test for chemical agents or conditions that effect retrotransposition. A single-step test was developed by replica plating cells containing pGTy1-H3mHIS3AI onto SC-ura galactose plates that contain limiting amounts of histidine (FIG. 4). These plates select for maintenance of the plasmid and induce transcription of the marked element. However, growth of the cells beyond a few generations cannot occur unless they become His+ by transposition of the spliced TymHIS3 element. Induction of pGTy1-H3mHIS3AI transcription in limiting histidine medium results in a large number of histidine prototrophs. As expected, repressing pGTy1-H3mHIS3AI, transcription by plating on glucose blocks growth because there is no transposition of the marked element.

Figure 3:
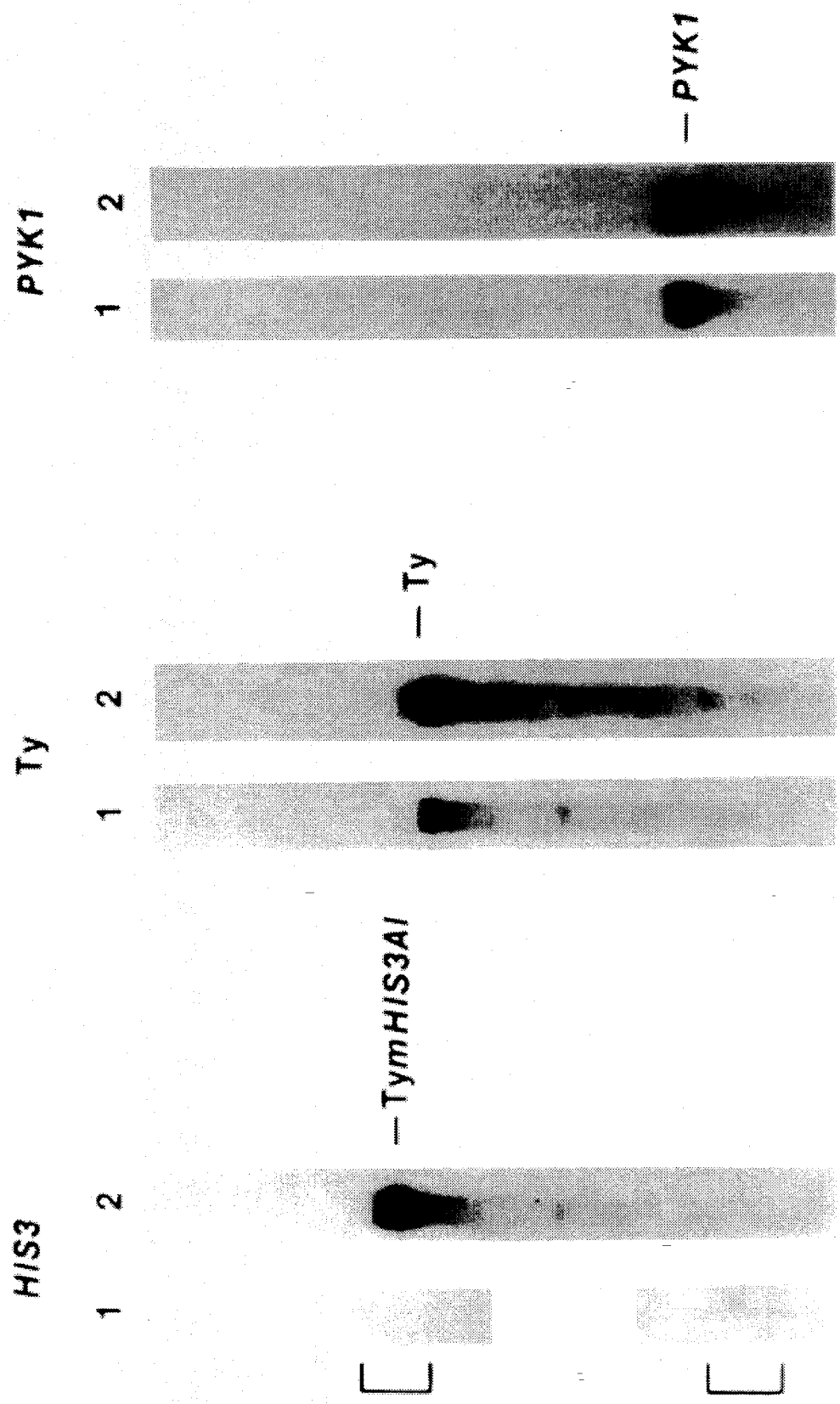
FIG. 3. Northern blot analysis of two strains each containing a single genomic TymHIS3AI element. A Northern blot containing 5 µg of total RNA from strains JC234 (lane 1) and JC242 (lane 2) was sequentially hybridized with HIS3, Ty1, and PYK1 probes. A longer exposure of the bracketed region of lane 1, required to detect the TymHIS3AI transcript in strain JC234, is shown below in lane 1.

To determine whether the single-step retrotransposition test could be used to demonstrate the inhibition of transposition, induction of pGTy1-H3mHIS3AI was compared at semipermissive (30° C.) or nonpermissive (37° C.) temperatures (Paquin, C. E., et al. Science (1984) 224:53–55; D. J. G., unpublished results). As shown in FIG. 3, no His+ revertants resulted from galactose induction of the pGTy1-H3mHIS3 element at 37° C. This is not due to temperature-dependent expression of the HIS3 gene, since a strain containing a transposed copy of TymHIS3 grew well at 37° C.

EXAMPLE 7

Detection of Retrotransposition Inhibitors.

Figure 5B:
FIG. 5. Hydroxyurea inhibits Ty transposition. Approximately 1×10⁷ cells harboring the plasmid pGTy1-H3mHISAI were plated onto growth media containing galactose and lacking uracil. The plate in panel A lacks histidine, which only supports growth of cells that have undergone transposition of the Ty1-H3mHISAI element; the plate in panel B contains histidine, which supports the growth of all cells. Filters saturated with a 2M solution of hydroxyurea were added to the plates. Plates were incubated for 3 days at 30° C. and then photographed. The histidine-dependent zone of inhibition indicates that hydroxyurea inhibits Ty transposition but not growth of yeast cells.
Figure 5A:

The above-described assay was used to show that the antineoplastic agent hydroxyurea markedly inhibits Ty transposition (FIG. 5). The zone of inhibition surrounding the area of where hydroxyurea was applied is dependent on the presence of histidine in the medium (FIG. 5, plate A). The absence of a zone of inhibition on plates containing histidine indicates that hydroxyurea does not markedly inhibit growth of the yeast cells under the conditions used in this experiment (FIG. 5, plate B).

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A vector comprising a DNA segment comprising a selectable marker gene wherein said selectable marker gene contains an intron inserted into a coding sequence of said gene and said intron is present in an antisense orientation relative to transcription of said marker gene.

2. The DNA segment according to claim 1, wherein said selectable marker gene is HIS3 containing said intron.

3. The DNA segment according to claim 2, wherein said selectable marker gene is HIS3AI.

4. A cell that is transformed with a DNA segment according to claim 1.

5. A vector comprising a DNA segment comprising a selectable marker gene inserted into a retrotransposon wherein said selectable marker gene contains an intron inserted into a coding sequence of said gene and said intron is in an antisense orientation relative to transcription of said marker gene and in a sense orientation relative to transcription of said retrotransposon.

6. The DNA segment according to claim 5, wherein said intron is an artificial intron.

7. The DNA segment according to claim 6, wherein said artificial intron is a yeast artificial intron.

8. The DNA segment according to claim 7, wherein said yeast artificial intron is a 104-base-pair artificial yeast intron contained on a PvuII-SnaB1 fragment.

9. The DNA segment according to claim 5, wherein said selectable marker gene is HIS3 containing said intron.

10. The DNA segment according to claim 9, wherein said selectable marker gene is HIS3AI.

11. The DNA segment according to claim 10, wherein said DNA segment is Ty1-H3mHIS3A1.

12. The DNA segment according to claim 11, wherein said DNA segment is pGTy1-H3mHIS3A1.

13. The DNA segment according to claim 5, wherein said retrotransposon is a yeast retrotransposon.

14. The DNA segment according to claim 13, wherein said yeast retrotransposon is Ty1.

15. A cell that is transformed with a DNA segment according to claim 5.

16. The cell according to claim 15, wherein said cell is a eukaryotic cell.

17. The cell according to claim 16, wherein said eukaryotic cell is a yeast cell.

* * * * *